United States Patent [19]
Robinson

[11] Patent Number: 5,787,908
[45] Date of Patent: *Aug. 4, 1998

[54] DENTAL FLOSSING APPARATUS

[76] Inventor: Dane Q. Robinson, 6015 E. Quartz Mountain Rd., Paradise Valley, Ariz. 85253

[*] Notice: The term of this patent shall not extend beyond the expiration date of Pat. No. 5,573,020.

[21] Appl. No.: 637,501

[22] Filed: Apr. 25, 1996

Related U.S. Application Data

[60] Division of Ser. No. 93,188, Jul. 16, 1993, Pat. No. 5,573,020, which is a continuation-in-part of Ser. No. 1,521, Jan. 7, 1993, abandoned.

[51] Int. Cl.$^6$ ............................................. A61C 15/00
[52] U.S. Cl. ........................... 132/322; 433/118; 433/143
[58] Field of Search ................................. 132/321, 322, 132/323, 324; 433/82, 118, 141, 142, 143; 601/139, 141, 142, 162

[56] References Cited

U.S. PATENT DOCUMENTS

| | | | |
|---|---|---|---|
| Re. 30,536 | 3/1981 | Perdreaux, Jr. | 433/86 |
| 2,931,371 | 4/1960 | Petitta | 132/324 |
| 3,472,045 | 10/1969 | Nelson et al. | 433/141 |
| 3,552,022 | 1/1971 | Axelsson | 32/58 |
| 3,559,292 | 2/1971 | Weissman | 433/141 |
| 3,563,233 | 2/1971 | Bodine | 128/36 |
| 3,660,902 | 5/1972 | Axelsson | |
| 3,672,378 | 6/1972 | Silverman | 132/329 |
| 3,809,977 | 5/1974 | Balamuth et al. | 318/116 |
| 3,902,510 | 9/1975 | Roth | 132/322 |
| 3,967,617 | 7/1976 | Krolik | 128/36 |
| 4,004,344 | 1/1977 | Gold et al. | 32/27 |
| 4,019,522 | 4/1977 | Elbreder | 132/322 |
| 4,048,723 | 9/1977 | Thorup | 433/82 |
| 4,205,664 | 6/1980 | Baccialon | 128/62 A |
| 4,235,253 | 11/1980 | Moore | 132/92 R |
| 4,319,377 | 3/1982 | Tarrson et al. | |
| 4,319,593 | 3/1982 | Ulrich | 132/322 |
| 4,326,547 | 4/1982 | Verplank | 132/89 |
| 4,347,839 | 9/1982 | Youngclaus, Jr. | 128/62 A |
| 4,397,327 | 8/1983 | Hadary | |
| 4,577,649 | 3/1986 | Shimenkov | 132/329 |
| 4,608,019 | 8/1986 | Kumabe et al. | 433/118 |
| 4,634,376 | 1/1987 | Mossle et al. | 433/118 |
| 4,791,940 | 12/1988 | Hirshfeld et al. | 433/141 |
| 4,820,154 | 4/1989 | Römhild et al. | 433/128 |
| 4,832,063 | 5/1989 | Smole | 132/329 |
| 4,913,133 | 4/1990 | Tichy | 128/62 A |
| 4,922,936 | 5/1990 | Buzzi et al. | 132/329 |
| 4,995,403 | 2/1991 | Beckman et al. | 433/118 |
| 5,000,684 | 3/1991 | Odrich | 433/125 |
| 5,002,487 | 3/1991 | Tichy | 433/122 |
| 5,050,625 | 9/1991 | Siekmann | 132/323 |
| 5,069,621 | 12/1991 | Paradis | 132/321 |
| 5,071,348 | 12/1991 | Woog | 433/118 |
| 5,100,321 | 3/1992 | Coss et al. | 433/118 |
| 5,123,841 | 6/1992 | Millner | 433/125 |
| 5,125,837 | 6/1992 | Warrin et al. | 433/98 |
| 5,224,500 | 7/1993 | Stella | 132/322 |
| 5,236,358 | 8/1993 | Sieffert | 433/119 |
| 5,293,886 | 3/1994 | Czapor | 132/329 |
| 5,419,703 | 5/1995 | Warrin et al. | 423/216 |
| 5,573,020 | 11/1996 | Robinson | 132/322 |

FOREIGN PATENT DOCUMENTS

| | | | |
|---|---|---|---|
| 0 354 352 | 2/1990 | European Pat. Off. | A61C 15/02 |
| 42 26 659 | 2/1994 | Germany . | |
| 43 09 078 | 9/1994 | Germany . | |
| WO 94/04093 | 3/1994 | WIPO | A61C 15/00 |

*Primary Examiner*—Todd E. Manahan
*Attorney, Agent, or Firm*—Seed and Berry LLP

[57] ABSTRACT

An electro-mechanical dental flossing device is disclosed for flossing the area between a portion of the tooth and the gum tissue. The device comprises an elongated member coupled to a motor source to effect oscillation of the elongated member. The elongated member includes an intermediate portion and a tip which are capable of being received between the tooth and the gum tissue.

102 Claims, 3 Drawing Sheets

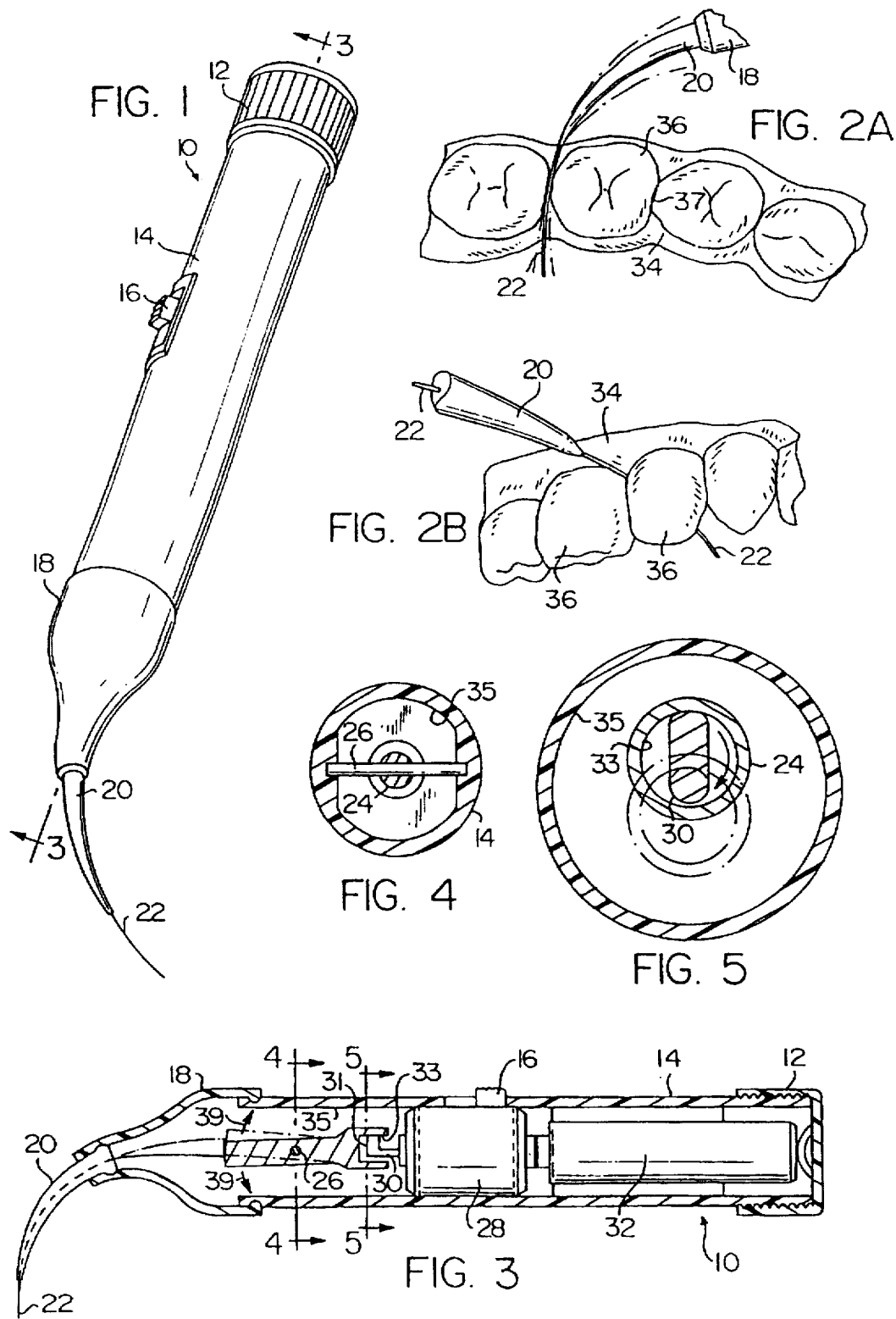

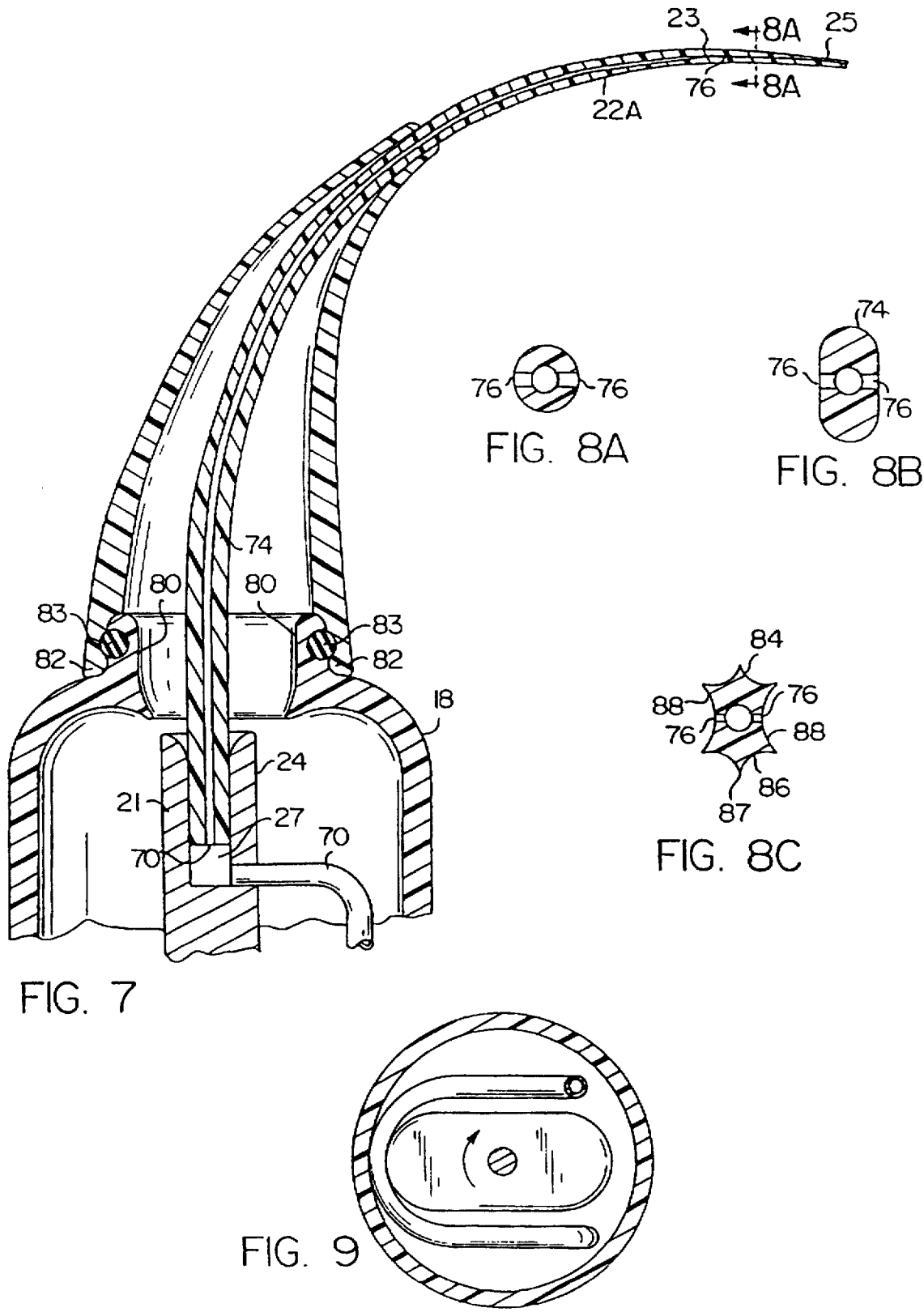

DENTAL FLOSSING APPARATUS

CROSS-REFERENCE TO RELATED APPLICATIONS

This is a divisional of U.S. patent application Ser. No. 08/093,188, filed Jul. 16, 1993, now U.S. Pat. No. 5,573,020, which is a continuation-in-part of U.S. patent application Ser. No. 08/001,521, filed Jan. 7, 1993, now abandoned.

FIELD OF INVENTION

This invention generally relates to dental devices and methods, and, more specifically, to an electromechanical dental flossing device and method therefor which provides a hand held, electrically powered flossing tool having a tip comprised of a substantially thin, flexible member capable of being received between a tooth and the adjacent interdental papilla portion of the gum (the dental sulcus). The tip is oscillated to produce a flossing action.

DESCRIPTION OF PRIOR ART

The prior art provided various types of dental devices and methods for the cleaning of teeth as well as the massaging of the gum tissue. For example, U.S. Pat. No. Re. 30,536, "Ultrasonic Device and Method", issued on Mar. 3, 1981 shows an apparatus which utilizes an ultrasonically driven head in conjunction with a spray of liquid or slurry containing abrasive material to operate as a cutting or cleaning tool in dental operations. As a second example, U.S. Pat. No. 4,913,133, "Hand Held Periodontic Tool", issued on Apr. 3, 1990 discloses a hand held periodontic tool which vibrates a flexible tip for use in massaging gum tissue, but which cannot be used for dental flossing. Such prior art devices, however, are typically unable to reach the area between the portion of the tooth located beneath the gum tissue surface and the gum tissue itself (interdental papilla). This area was generally cleaned with dental floss.

However, the use of dental floss can be somewhat cumbersome. In many instances there are contact areas between the teeth (i.e. portions of the crowns of the teeth are closely adjacent or touching), typically at the top of the crown. In order for floss to be received between the teeth, it is generally necessary for the floss to be forced between the teeth from above, and must pass through any contact area. However, such contact areas often do not provide adequate space to permit passage of the floss. This tends to result in the floss shredding or breaking rather than passing between the teeth. In such instances, some manner of threading device must be employed.

Devices which dispose a strand of floss between rigid arms of a forked or "U" shaped tip to facilitate flossing are available. Electrical flossing devices which reciprocate such a tip are also known. An example of such a device is described in U.S. Pat. No. 4,235,253, issued Nov. 25, 1980, to D. A. Moore.

Thus, although the prior art discloses a variety of devices for the cleaning of the exposed surfaces of the teeth and for the massaging of the gum tissue, and devices to facilitate flossing, there remains a need for a device to more effectively and efficiently clean or floss the area not only between the teeth, but also the area between the interdental papilla and the interproximal surface of the tooth.

SUMMARY OF INVENTION

The present invention provides an improved electromechanical dental flossing device and method therefor which effectively and efficiently provides a flossing action both between and around teeth as well as providing a flossing action between the portion of the tooth that is beneath the gum tissue surface adjacent to the interdental papilla.

In accordance with one aspect of the present invention an electromechanical dental flossing device employs a thin and flexible elongated member capable of being at least partly received between a tooth and the adjacent interdental papilla portion of the gum. The device employs a motive source to effect motion of the elongated member by way of a coupling.

In accordance with another aspect of the invention, the elongated member manifests a predetermined cross-section. In accordance with various aspects of the invention, the member may have: a generally circular cross-section with a diameter no greater than approximately 0.025 inch; a generally elliptical cross-section with a minor diameter no greater than approximately 0.025 inch; a cross-section generally circumscribed by a top, a bottom and inwardly concave arcuate sides when the maximum transverse distance between corresponding points of the side is no greater than approximately 0.025 inch.

In accordance with another aspect of the invention, the motive source is a motor which includes a shaft with an eccentric member mounted thereon. The coupling has a translation member connected to the elongated member and an axial aperture which receives the eccentric member. Rotation of the eccentric member causes repetitive translation of the coupling and the elongated member. Alternatively, flossing motion of the elongated member is effected by connecting the base of the elongated member directly to the motor shaft or eccentric.

In accordance with another aspect of the invention, the elongated member includes a conduit. The conduit is in communication with a fluid reservoir and with an orifice in the surface of the elongated member. A pump is disposed to propel fluid from the reservoir through the conduit to the orifice.

BRIEF DESCRIPTION OF THE DRAWING

The preferred exemplary embodiment of the present invention will hereinafter be described in conjunction with the appended drawing, wherein like designations denote like elements, and:

FIG. 1 is a perspective drawing of a first embodiment of a flossing device in accordance with this invention;

FIG. 2A is an elevational view showing the elongated member of the device of FIG. 1 flossing the area between two teeth;

FIG. 2B is front perspective view showing the elongated member of the device of FIG. 1 flossing the area between a portion of a tooth that is beneath the gum tissue surface and the gum tissue itself;

FIG. 3 is a cross sectional view of the flossing device of FIG. 1 taken along the line 3—3 of FIG. 1;

FIG. 4 is a cross sectional view of device of FIG. 1 taken along the line 4—4 of FIG. 3;

FIG. 5 is a cross sectional view of the device of FIG. 1 taken along the line 5—5 of FIG. 3;

FIG. 7 is an expanded view of the tip of the device of FIG. 6;

FIGS. 8A–C are cross sectional views of various embodiments of an elongated member taken along line 8—8 of FIG. 7; and FIG. 9 is a cross-sectional view of the device of FIG. 6 taken along line 9—9 showing a preferred embodiment of a pump.

DESCRIPTION OF THE PREFERRED EMBODIMENT

Figure 3A:
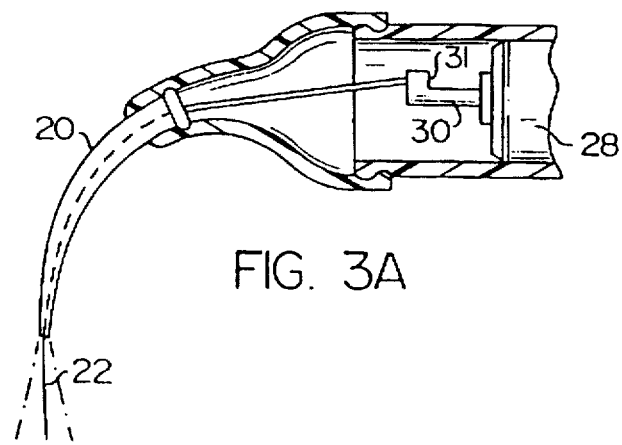
FIG. 3A is a partial cross sectional view of an alternative embodiment of a mechanism for effecting motion of the elongated element in a flossing device in accordance with the present invention.

Referring to FIGS. 1 and 3, an electro-mechanical dental flossing device 10 in accordance with the present invention suitably comprises a lower cap 12, a case 14, a generally conical tip 18, enclosing a power source 32 (e.g. battery), a motor 28, a switch 16, an elongated member 22, and a mechanism coupling member 22 to motor 28. The coupling mechanism suitably includes a translation member 24 pivotally mounted within case 14. Lower cap 12 is removably fixed to one end of case 14. Electrical control switch 16 extends through the sidewall of case 14. Conical tip 18, suitably formed of a resilient material such as a polymer or rubber composition, is attached, preferably removably, to the opposite end of flossing device case 14. Elongated member 22 extends through a rubber insert 20, which is disposed within tip 18 as shown in FIG. 3.

Elongated member 22 includes a base portion 21, an intermediate portion 23 and a tip portion 25. As will be more fully discussed, at least intermediate portion 23, and preferably also tip portion 25 are configured to be received between the teeth and the interdental papilla. Elongated member 22 can be made of any material suitable for use in the human mouth which is flexible and resilient. Suitable materials can include plastics, metal wire, textiles and the like which are flexible, have a memory and are impregnable to the environment of the mouth. For example, elongated member 22 may comprise a Nickel-Titanium alloy wire, having a diameter on the order of about 0.010 inches to about 0.025 inches. In some cases, a protective coating of plastic or other insulator, such as, but not limited to, TEFLON™ may also be employed.

If desired, elongated member 22, or a protective coating, or both can be impregnated with a diffusant, such as a medicament, e.g. fluoride, a fluoride release, a germicide, or an antibacterial release, or a flavor, such as mint or cinnamon. As will hereafter be described, fluids such as, for example, medicaments and mouthwash, can also be applied to the user's teeth and gums through member 22A.

Referring to FIG. 3, power source 32, which is preferably a battery, is electrically coupled to electric motor 28. Motor 28 is selectively energized by power source 32 through switch 16.

Motor 28 is employed to oscillate elongated member 22. Motor 28 includes an axially protruding arm 30 which rotates when motor 28 is energized. The distal end of axial arm 30 includes an eccentric 31 (e.g. cam) disposed to penetrate an axial aperture 33 on one end of motion translation member 24. Base 21 of elongated member 22 is secured to the opposite end of translation member 24. Preferably, base 21 received in an axial bore 27 in translation member 24. Base 21 is preferably removably engaged by friction fit, or otherwise secured in bore 27. Motion translation member 24 is free to oscillate about a pin 26 which is fixedly attached to an inner wall 35 of case 14.

Flossing device 10 provides a particularly convenient mechanism for effectively and efficiently accessing not only the tooth surfaces between the teeth for cleaning and application of fluids, but also the sulcus between the interdental papilla portions of the gum and the teeth, irrespective of contact areas between the teeth. Referring to FIGS. 2A and 2B, the human mouth includes a plurality of adjacent teeth 36 disposed in the gums 34. Each tooth typically includes a crown (body) portion projecting above the gum, a root connecting the tooth to bone, and a constricted neck portion between the root and crown surrounded by the gums. In many instances, the relative dispositions of adjacent teeth 36 create contact areas 37 between the crowns of the teeth, i.e., portions of the crowns of adjacent teeth touch or nearly touch. In many such instances, contact areas make access to the sulcus between interdental papilla and the neck of the tooth from above, as conventionally required, particularly difficult, if not impossible. Tip 25 and intermediate portion 23 of elongated member 22 are dimensioned and configured to be received between teeth 36 (FIG. 2A). Intermediate portion 23 and, preferably tip 25, are also dimensioned and configured to be received in the sulcus between interdental papilla and tooth (FIG. 2B). However, elongated member 22, while resilient, is sufficiently stiff to maintain its shape, and thus is capable of being inserted into the area between teeth 36 and ultimately within the sulcus, irrespective of contact areas 37 by passing between teeth 36 from the labial (front) or lingual (back) directions below the contact areas. A flossing action is realized through motion of member 22 with member 22 situated as shown in FIGS. 2A and 2B.

Referring to FIG. 4, motion translation member 24 is fixedly attached to inner wall 35 of flossing device case 14 by pin 26. When flossing device 10 is in operation, motion translation member 24 oscillates about fixed pin 26 as shown by arrows 39 in FIG. 3.

Referring to FIG. 5, eccentric 31 on arm 30 is received within axial aperture 33 of motion translation member 24. When rotated, protective periphery of eccentric 31 effective moves about an axis that is off-set from the axial center of motion translation member 24 such that the rotation of eccentric 31 produces an oscillatory motion of motion translation member 24 about pin 26. Thus, rotation of the axial arm 30, through operating electric motor 28, causes an oscillation motion (as shown by the arrows 39) of motion translation member 24.

In operation, electric switch 16 completes the electrical circuit to energize electric motor 28 from power supply 32. If desired, switch 16 can have multiple settings for different oscillation speeds of motor 28. While operating, electric motor 28 rotates axial arm 30. The rotation of eccentric 31 by axial arm 30 within axial aperture 33 of motion translation member 24 causes the oscillatory motion of the motion translation member 24 about fixed pin 26. Due to the rapid oscillation of motion translation member 24, elongated member 22 oscillates to produce the desired flossing action between two teeth 36 or between a tooth 36 and gum portion 34.

The desired flossing motion can be imparted to elongated member 22 in numerous ways in addition to the mechanism described above. For example, as shown FIG. 3A, in an alternative embodiment, translation member 24 can be omitted and the base of member 22 can be directly connected to the distal end of motor arm 30, e.g. to eccentric 31. As a consequence of the arcuate disposition of elongated member 22 with respect to the axis of motor arm 30, and the interaction of member 22 with e.g. tip 18, rotation of arm 30 will cause member 22 to effect movement with both rotational and translatory components, e.g. to effectively precess as generally indicated in dotted line in FIG. 3A. The translatory component of such motion is of greater magnitude if the base of member 22 is attached to motor arm 30 offset from the central axis of arm 30, e.g. in the vicinity of the periphery of eccentric 31.

Figure 6:
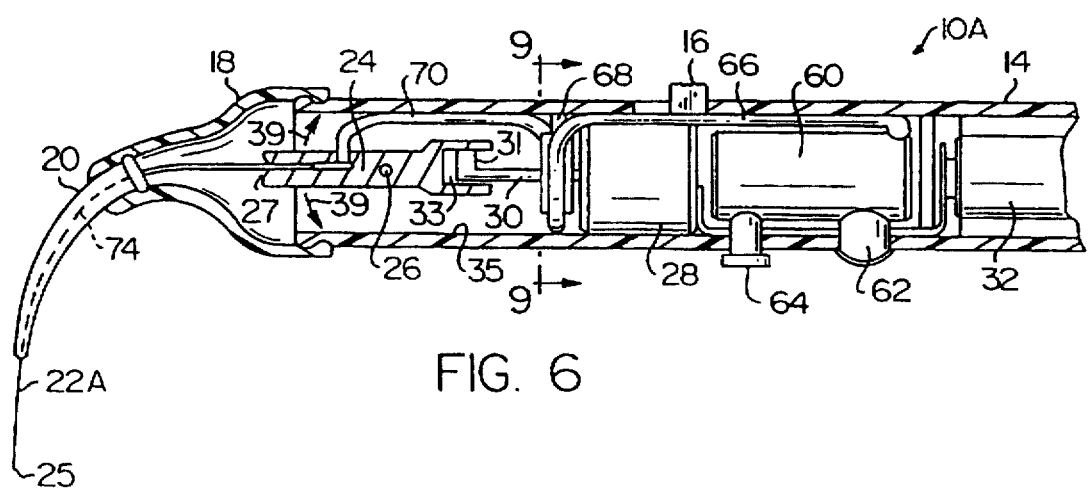
FIG. 6 is a cross section view of an alternative embodiment of the flossing device of FIG. 1 taken along line 3—3 of FIG. 1 and including a fluid reservoir and a pump.

Referring now to FIG. 6, an alternative embodiment of a flossing device 10A includes provisions for applying fluids such as medicaments to the gums and teeth. Flossing device 10A suitably includes, in addition to the components previously described in conjunction with FIGS. 1 through 5, a fluid reservoir 60, a pump 68, and respective conduits 66 and 70 providing communication between reservoir 60, pump 68, and ultimately elongated member 22. As will be discussed, in this embodiment, elongated member 22 includes an axial conduit and apertures for delivering the fluid to the user's teeth and gums. Fluid reservoir 60 is suitably a collapsible polymeric bag, having a capacity of from about two to four liquid ounces. If desired, reservoir 60 can be refillable communicating with capped filling orifice 64 extending through the sidewall of casing 14. Alternatively, reservoir 60 can be disposable, removably received within casing 14 and releasably coupled to conduit 66. Fluid reservoir 60 may be any vessel capable of containing fluid and dispensing it through conduit 66. Reservoir 60 is preferably configured to be disposed within casing 14. However, if desired, conduit 66 can be channeled through the sidewall of casing 14 and cooperate with an external reservoir. In this case, reservoir 60 would be purchased prefilled with the medicament or other fluid to be applied to the user's teeth and gums, made to communicate with conduit 66 and received within casing 14. Communication with conduit 66 can be effected in any convenient manner, such as, for example, a nipple which is punctured and received within the end of conduit 66, a fixture on the end of conduit 66 which punctures a resilient portion of reservoir 60 or cooperating fittings, or the like, applying fluids such as medicaments, bactericides, germicides, fluorine treatments, mouthwash or the like to the user's teeth and gums.

If desired a level indicating mechanism can be provided. For example, reservoir 60 may be formed of a translucent or transparent material, and a window 62 provided in the side wall of casing 14.

Referring now to FIG. 6 and 7, elongated member 22A includes an axial conduit 74 communicating between a first orifice 72 in base portion 21, and at least one small orifice 76 disposed in either intermediate portion 23 or tip portion 25, as will be explained. Preferably, numerous small orifices are provided in intermediate portion 23, communicating between the sidewall of intermediate portion 23 and conduit 74.

Conduit 70 is coupled to elongated element conduit 74. The coupling may be effected by any mechanism consistent with the movement of element 22A effected by translation member 24. Preferably, as in the embodiment of FIGS. 1 through 5, base 21 of elongated member 22A is received in a friction fit in an axial bore 27 in translation member 24. Preferably, the communication is effected through translation member 24. A transverse channel 75 is formed, extending from axial bore 27 through the sidewall of member 24, and is configured to closely receive and retain the end of conduit 70. Conduit 70 is preferably formed of resilient material, and enough slack is provided to permit the desired movement of member 24 and elongated element 22a.

In operation, pump 68 draws a fluid from reservoir 60 causing it to flow through conduits 66, 70, and 74, so that it is ultimately dispensed through orifices 76 elongated member 22A. Pump 68 may be any device suitable for effecting that function, preferably driven by motor 28. Referring to FIGS. 6 and 9, a particularly advantageous pump 68 employs a cam or eccentric 90 disposed for rotation on arm 30. A flexible conduit 92, coupling conduits 66 and 70 is disposed for cooperation with the periphery of eccentric 90. A retainer 94, suitably in the form of an annulus, may be employed to ensure proper disposition of conduit 92 relative to eccentric 90. Eccentric member 90 is suitably elliptical in shape. When rotated, the periphery of eccentric 90 in the vicinity of the long axis, partially collapses or otherwise distorts conduit 92, drawing fluid from reservoir 60 and urging the fluid in conduit 92 into conduit 70, and ultimately to orifices 76. If desired, conduits 66, 92, and 70, can be formed of a single length of resilient, e.g., polymeric, tubing.

If desired, particularly where replaceable elongated members 22, 22A are employed, tip 18 may be removably connected to casing 14 to facilitate replacement of elongated member 22, 22A. The connection is preferably water tight. Referring to FIG. 7, respective collars 80 and 82, are formed on the upper periphery of casing 14, and lower inner periphery of tip 18, respectively. The inside diameter of the base of tip 18 is slightly larger than that of collar 80. Collars 80 and 82 are resilient enough that collar 82 will snap over collar 80. In addition, a flexible O-ring 83 can be employed if desired.

Intermediate portion 23, and preferably tip 25, may manifest any cross section in accordance with the present invention so long as it may be received between the inter-dental papilla portion of the gums and an adjacent tooth. The cross section can be consistent along its length, or may vary with length. In the simplest case, as shown in FIG. 8A, a circular cross section can be employed. The diameter of the cross section is sufficiently small to be received between inter-dental papilla and tooth, e.g., no greater than about 0.025-inch. Similarly, as shown in FIG. 8B, all or a part of intermediate portion 23 may manifest an elliptical cross section having a minor diameter that is sufficiently small so that it can be received between inter-dental papilla and adjacent tooth, e.g., no greater than 0.025-inch. In each instance, axial conduit 74, and orifices 76 communicating with axial bore 74 are preferably provided.

However, more complex cross sections can be advantageously employed. For example, referring to FIG. 8C, one embodiment of intermediate portion 23 of elongated member 22a in accordance with the present invention has a cross-section circumscribed by a top 84, a bottom 86 and respective sides 88. Sides 88 are suitably arcuate, namely, inwardly directed concave arcs. Orifices 76 are situated in the narrow waist of sides 88. In accordance with the preferred embodiment, the maximum transverse distance between corresponding points on sides 84 is sufficiently small so that intermediate portion 23 can be accommodated between the interdental papilla portion of the gum and the surface of the adjacent tooth, e.g., is no greater than about 0.025 inch. Bottom 86 also suitably converges to a point 87. Thus, while the invention has been particularly shown and described with reference to the preferred embodiment thereof, it will be understood by those skilled in the art that the foregoing and other changes in form and details may be made therein without departing from the spirit and scope of the invention.

I claim:

1. Apparatus for cleaning the surfaces of teeth underlying the inter-dental papilla portion of the gums in a human mouth by effecting a flossing action, comprising:

a flexible, resilient, non-abrasive elongated member;
   said elongated member including a base portion, an elongated intermediate portion of predetermined cross-sectional configuration, and a tip;

said intermediate portion and said tip being sized to be received between adjacent teeth without traversing any contact areas between the teeth from at least the front of the mouth and being sufficiently flexible and resilient to effect the flossing action therebetween by imparting a flossing motion to said intermediate portion; and at least the intermediate portion being sized to be received in the sulcus between a tooth and the adjacent interdental papilla portion of the gum for effecting the flossing action therebetween;

a handle; and a coupling releasably connecting the base portion of the elongated member to the handle, said coupling applying a moving force to said elongated member with at least one of a translational and a rotational component to impart said flossing motion to said intermediate portion.

2. The apparatus of claim 1, wherein both said intermediate portion and said tip are sized to be received in the sulcus between a tooth and the adjacent inter-dental papilla portion of the gum.

3. The apparatus of claim 1, wherein said intermediate portion has a generally circular cross-section and a diameter no greater than approximately 0.025 inch.

4. The apparatus of claim 1, wherein said intermediate portion has a generally elliptical cross-section with a minor diameter no greater than approximately 0.025 inch.

5. The apparatus of claim 1, wherein said coupling comprises an aperture configured to receive said elongated member base portion.

6. The apparatus of claim 1, wherein said intermediate portion has a cross-section circumscribed by a top, a bottom, and respective sides, and at least said sides are arcuate.

7. The apparatus of claim 6, wherein said arcuate sides are each inwardly directed concave.

8. The apparatus of claim 7 wherein the maximum transverse distance between corresponding points on said sides is no greater than approximately 0.025 inch.

9. The apparatus of claim 6 wherein said bottom converges to a point.

10. The apparatus of claim 1, wherein said intermediate portion has a generally circular cross-section.

11. The apparatus of claim 1, wherein said intermediate portion has a generally elliptical cross-section.

12. The apparatus of claim 1, wherein said intermediate portion has a cross-section circumscribed by a top, a bottom, and respective sides, and wherein said bottom converges to a point.

13. The apparatus of claim 1, wherein at least a portion of one of said intermediate portion and said tip are impregnated with a diffusant.

14. The apparatus of claim 1, wherein at least a portion of one of said intermediate portion and said tip are impregnated with a medicament.

15. The apparatus of claim 14, wherein said medicament is chosen from the class consisting of fluoride, fluoride releases, germicides, and anti-bacterial releases.

16. The apparatus of claim 1, wherein at least a portion of one of said intermediate portion and said tip are impregnated with a flavor.

17. The apparatus of claim 1, wherein said intermediate portion has a cross-section circumscribed by a top, a bottom, and respective sides, and wherein the maximum transverse distance between said sides is no greater than approximately 0.025 inch.

18. The apparatus of claim 1, wherein said coupling is detachably connected to said elongated member.

19. The apparatus of claim 18 wherein said coupling includes an aperture configured to receive said elongated member base portion.

20. Apparatus for cleaning the surfaces of teeth underlying the inter-dental papilla portion of the gums in a human mouth by effecting a flossing action, comprising:

a flexible, resilient, non-abrasive flossing filament;

said flossing filament including a base portion, a free-end portion, and an elongated intermediate portion located between said base portion and said free-end portion;

said intermediate portion and said free-end portion being sized to be received between adjacent teeth without traversing any contact areas between the teeth from at least the front of the mouth, at least said intermediate portion having sufficient flexibility and resiliency to effect the flossing action therebetween by imparting a flossing motion to said intermediate portion, said intermediate portion extending along a longitudinal line when not moving;

at least said intermediate portion being sized to be received in the sulcus between a tooth and the adjacent inter-dental papilla portion of the gum for effecting the flossing action therein;

a motive source; and a coupling connecting said base portion of said flossing filament to said motive source and moving said flossing filament with a component of motion out of alignment with said longitudinal line to impart said flossing motion to said intermediate portion in response to operation of said motive source.

21. The apparatus of claim 20 wherein said motive source produces an output drive and said coupling translates said output drive into an oscillatory drive and supplies said oscillatory drive to said base portion to move said flossing filament with said component of motion out of alignment with said longitudinal line and produce said flossing motion of said intermediate portion.

22. The apparatus of claim 20, wherein said intermediate portion has sufficient length to extend from the front of the mouth between and rearward beyond adjacent teeth.

23. The apparatus of claim 20, wherein said motive source is a motor.

24. The apparatus of claim 23, wherein said motor is an electric motor.

25. The apparatus of claim 23, wherein said motor produces a rotational output drive and said coupling converts said rotational output drive into a moving force with a force component out of alignment with said longitudinal line to produce said component of motion out of alignment with said longitudinal line.

26. Apparatus for cleaning the surfaces of teeth underlying the inter-dental papilla portion of the gums in a human mouth by effecting a flossing action, comprising:

a flexible, resilient flossing filament;

said flossing filament including a base portion, a free-end portion, and a non-abrasive elongated intermediate portion located between said base portion and said free-end portion;

said intermediate portion and said free-end portion being capable of being received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion, said intermediate portion extending along a longitudinal line when not moving;

at least said intermediate portion being capable of being received in the sulcus between a tooth and the adjacent inter-dental papilla portion of the gum for effecting the flossing action therein;

a motive source; and a coupling connecting said flossing filament to said motive source and moving said flossing filament with a component of motion out of alignment with said longitudinal line to impart said flossing motion to said intermediate portion.

27. The apparatus of claim 26 wherein said motive source produces an output drive and said coupling translates said output drive into an oscillatory drive and supplies said oscillatory drive to said flossing filament to move said flossing filament with said component of motion out of alignment with said longitudinal line and produce said flossing motion of said intermediate portion.

28. The apparatus of claim 26 wherein said intermediate portion of said flossing filament has an elongated tooth engagement portion with a uniform cross-sectional size and shape along its length.

29. The apparatus of claim 28 wherein said elongated tooth engagement portion of said intermediate portion has a circular cross-sectional shape along its length.

30. The apparatus of claim 29 wherein said circular cross-section of said elongated tooth engagement portion has a diameter no greater than approximately 0.025 inch.

31. The apparatus of claim 26 wherein said intermediate portion of said flossing filament has an elongated tooth engagement portion with a uniform cross-sectional shape along its length.

32. The apparatus of claim 31 wherein said elongated tooth engagement portion of said intermediate portion has a circular cross-sectional shape along its length.

33. The apparatus of claim 32 wherein said circular cross-sectional shape of said elongated tooth engagement portion has a diameter no greater than approximately 0.025 inch.

34. The apparatus of claim 26 wherein said intermediate portion of said flossing filament has an elongated tooth engagement portion with a cross-sectional size no greater than approximately 0.025 inch across.

35. The apparatus of claim 26, further including an elongated housing containing said motive source and said coupling with an exterior sized for grasping by the hand of a user, said motive source being positioned within a first end portion of said housing toward a first end thereof and said flossing filament extending generally coaxially through a second end portion of said housing toward a second end thereof, said flossing filament exiting said housing at said second end and having said free-end portion and an elongated tooth engagement portion of said intermediate portion located exterior of said housing for engagement with the tooth when said motive source is operating.

36. The apparatus of claim 35, further including a filament support positioned at said second end of said housing to support said flossing filament and having a passageway therethrough with said flossing filament extending through said passageway and movably disposed therein.

37. The apparatus of claim 36 wherein said filament support is positioned and supports said flossing filament at a location between said free-end portion and said base portion of said flossing filament.

38. The apparatus of claim 36 wherein said filament support has a curved portion and said passageway within said curved portion is correspondingly curved.

39. The apparatus of claim 36 wherein said filament support is removably attached to said housing.

40. The apparatus of claim 26 wherein said motive source provides driving movement of said flossing filament to produce said flossing movement of said intermediate portion, and the apparatus further includes a filament support positioned between said free-end portion and said base portion of said flossing filament to support said flossing filament at a location therealong, said free-end portion and an elongated portion of said intermediate portion extending beyond said filament support for engagement with the tooth when said motive source is operating.

41. The apparatus of claim 26 wherein said flossing filament has sufficient flexibility to bend under the force applied thereto resulting from movement of said flossing filament by said motive source to produce said flossing motion of said intermediate portion.

42. Apparatus for cleaning the surfaces of teeth underlying the inter-dental papilla portion of the gums in a human mouth by effecting a flossing action, comprising:

a flexible, resilient flossing filament;

said flossing filament including a base portion, a free-end portion, and a non-abrasive elongated intermediate portion located between said base portion and said free-end portion;

said intermediate portion and said free-end portion being capable of being received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;

at least said intermediate portion being capable of being received in the sulcus between a tooth and the adjacent inter-dental papilla portion of the gum for effecting the flossing action therein:

a motive source, said motive source rotatably connected by said coupling to said flossing filament to provide rotational drive to said flossing filament to produce said flossing motion of said intermediate portion; and a coupling connecting said flossing filament to said motive source to impart said flossing motion to said intermediate portion.

43. The apparatus of claim 42 wherein said motive source includes a drive shaft and said coupling connects said base portion of said flossing filament to said drive shaft in generally coaxial alignment therewith.

44. The apparatus of claim 42 wherein said motive source provides a unidirectional rotational drive to said flossing filament to produce said flossing motion in response to operation of said motive source.

45. The apparatus of claim 42 wherein said motive source provides a non-reciprocating, unidirectional rotational drive to said flossing filament to produce said flossing motion in response to operation of said motive source.

46. The apparatus of claim 42 wherein said flossing filament is elongated with a longitudinal axis and the apparatus further includes a filament support positioned between said free-end portion and said base portion of said flossing filament to support said flossing filament for rotation about said longitudinal axis in response to said rotational drive provided thereto by said motive source, with said free-end portion and an elongated portion of said intermediate portion extending beyond said filament support for engagement with the tooth when said motive source is operating.

47. The apparatus of claim wherein said intermediate portion extending beyond said filament support has sufficient flexibility to bend outward under the centrifugal force thereon resulting from rotation of said flossing filament by said motive source.

48. The apparatus of claim 46 wherein said motive source is rotatably connected by said coupling to said base portion, and said intermediate portion extending beyond said filament support has sufficient flexibility to bend outward while rotating in response to the centrifugal force thereon resulting from rotation of said base portion by said motive source.

49. The apparatus of claim 46 wherein said filament support has a passageway therethrough, and said flossing filament extends and is movably disposed in said passageway.

50. The apparatus of claim 49, further including a housing containing said motive source and said coupling, and wherein said filament support is removably attached to said housing.

51. The apparatus of claim 46 wherein said filament support is elongated and has an axially extending passageway therethrough, and said flossing filament extends and is movably disposed in said passageway.

52. The apparatus of claim 51 wherein said filament support has a curved portion and said passageway within said curved portion is correspondingly curved.

53. The apparatus of claim 42 wherein said flossing filament has sufficient flexibility to bend outward under the centrifugal force thereon resulting from rotation of said flossing filament by said motive source to produce said flossing motion of said intermediate portion.

54. Apparatus for cleaning the surfaces of teeth underlying the inter-dental papilla portion of the gums in a human mouth by effecting a flossing action, comprising:

a flexible, resilient flossing filament;

said flossing filament including a base portion, a free-end portion, and a non-abrasive intermediate portion located between said base portion and said free-end portion;

said intermediate portion and said free-end portion being sized to be received between adjacent teeth without traversing any contact areas between the teeth from at least the front of the mouth and being configured to effect the flossing action therebetween;

at least said intermediate portion being sized to be received in the sulcus between a tooth and the adjacent inter-dental papilla portion of the gum for effecting the flossing action therein;

a motive source; and a coupling connecting said flossing filament to said motive source and applying a moving force to said flossing filament with a force component out of longitudinal alignment with said flossing filament to effect a flossing motion of said flossing filament.

55. The apparatus of claim 54, wherein said force component out of alignment with said flossing filament applied by said coupling includes at least one of a translational and a rotational component.

56. The apparatus of claim 54, wherein said motive source is a motor.

57. The apparatus of claim 56, wherein said motor produces a rotational output drive and said coupling converts said rotational output drive into said moving force applied to said flossing filament.

58. Apparatus for cleaning the surfaces of teeth underlying the inter-dental papilla portion of the gums in a human mouth by effecting a flossing action, comprising:

a flexible, resilient flossing filament;

said flossing filament including a base portion, a free-end portion, and a non-abrasive intermediate portion located between said base portion and said free-end portion;

said intermediate portion and said free-end portion being capable of being received between adjacent teeth without traversing any contact areas between the teeth from at least the front of the mouth, at least said intermediate portion having sufficient flexibility and resiliency to be capable of effecting the flossing action therebetween;

at least said intermediate portion being capable of being received in the sulcus between a tooth and the adjacent inter-dental papilla portion of the gum for effecting the flossing action therein;

a motive source; and a coupling connecting said flossing filament to said motive source to effect a flossing motion of said flossing filament with a component of motion out of longitudinal alignment with said flossing filament.

59. The apparatus of claim 58, wherein said motive source is a motor.

60. The apparatus of claim 59, wherein said motor produces a rotational output drive and said coupling converts said rotational output drive into a moving force with a force component out of longitudinal alignment with said flossing filament to produce said component of motion out of longitudinal alignment with said flossing filament.

61. The apparatus of claim 59, wherein said motor produces a rotational output drive and said coupling converts said rotational output drive into a moving force with at least one of a translational and a rotational component to produce said component of motion out of longitudinal alignment with said flossing filament.

62. Apparatus for cleaning the surfaces of teeth underlying the inter-dental papilla portion of the gums in a human mouth by effecting a flossing action, usable with a motive source and a coupling positioned within a housing having an aperture, the apparatus comprising:

a flexible, resilient flossing filament having sufficient stiffness to be self-supporting;

said flossing filament including a base portion, a free-end portion, and a non-abrasive elongated intermediate portion located between said base portion and said free-end portion;

said intermediate portion and said free-end portion being sized to be received between adjacent teeth without traversing any contact areas between the teeth from at least the front of the mouth, at least said intermediate portion having sufficient flexibility and resiliency to effect the flossing action therebetween without damage to the teeth when imparting a flossing motion to said intermediate portion;

at least said intermediate portion being sized to be received in the sulcus between a tooth and the adjacent inter-dental papilla portion of the gum for effecting the flossing action therein; and an end member having a first end portion configured for removable attachment to the housing at the housing aperture and a free second end portion, said end member having a first end aperture toward said first end portion communicating with the housing aperture and a second end aperture in said second end portion with a passageway extending between said first and second end apertures, said flossing filament being movably disposed in said end member passageway, said flossing filament extending through said second end aperture with said filament free-end portion and at least a portion of said intermediate portion positioned outward of said end member, and extending through said first end aperture with said filament base portion positioned within said housing when said first end portion of said end member is attached to the housing, said filament base portion being configured for releasable connection by the coupling to the motive source so that when so attached said flossing motion is imparted to at least said portion of said intermediate portion positioned outward of said end member in response to operation of the motive source.

63. The apparatus of claim 62, further including a seal positioned between said first end portion of said end member and the housing at the housing aperture to provide a water tight seal between said end member and the housing to restrict the flow of water into the housing aperture when said end member is attached to the housing.

64. The apparatus of claim 62 wherein said end member first end portion includes a tip member having a first end configured for removable attachment to the housing at the housing aperture and a second end, and said second end portion includes a curved end piece having a first end configured for removable attachment to said tip member second end and a free second end, said end member first end aperture being located in said first end of said removable end piece and said end member second end aperture being located in said free second end of said removable end piece.

65. The apparatus of claim 64 wherein said tip member first end forms an interior chamber sized to receive at least a portion of the coupling therein by which said filament base portion is releasably connected to the motive source.

66. A method for cleaning the surfaces of teeth underlying the inter-dental papilla portion of the gums in a human mouth by effecting a flossing action, comprising:

providing a motive source;

providing a flexible, resilient flossing filament having a base portion, a free-end portion, and a non-abrasive intermediate portion located between said base portion and said free-end portion, at least said intermediate portion having sufficient flexibility and resiliency to effect the flossing action between adjacent teeth by producing a flossing motion when driven by said motive source;

positioning said intermediate portion and said free-end portion between adjacent teeth without traversing any contact areas between the teeth from the front of the mouth;

positioning at least said intermediate portion in the sulcus between a tooth and the adjacent inter-dental papilla portion of the gum for effecting the flossing action therein; and driving said flossing filament with said motive source to produce said flossing motion of said intermediate portion.

67. The method of claim 66 wherein the step of driving said flossing filament includes moving said flossing filament with a rotational component to impart said flossing motion to said intermediate portion.

68. The method of claim 66, further including releasably connecting said base portion to said motive source using a coupling to effect said flossing motion of said intermediate portion prior to the step of driving said flossing filament.

69. The method of claim 68, further including detaching said base portion from said motive source and replacing said detached flossing filament with a new replacement flossing filament prior to the step of driving said replacement flossing filament with said motive source.

70. Apparatus for cleaning the surfaces of teeth underlying the inter-dental papilla portion of the gums in a human mouth by effecting a flossing action, comprising:

a flexible, resilient flossing filament;

said flossing filament including a base portion, a free-end portion, and a non-abrasive elongated intermediate portion located between said base portion and said free-end portion;

said intermediate portion and said free-end portion being capable of being received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;

at least said intermediate portion being capable of being received in the sulcus between a tooth and the adjacent inter-dental papilla portion of the gum for effecting the flossing action therein;

a motive source, a coupling connecting said flossing filament to said motive source to impart said flossing motion to said intermediate portion, said motive source being rotatably connected by said coupling to said flossing filament to rotate said flossing filament to produce said flossing motion;

an elongated housing containing said motive source and said coupling with an exterior sized for grasping by the hand of a user, said motive source being positioned within a first end portion of said housing toward a first end thereof and said flossing filament extending generally coaxially through a second end portion of said housing toward a second end thereof, said flossing filament exiting said housing at said second end and having said free-end portion and an elongated tooth engagement portion of said intermediate portion located exterior of said housing for engagement with the tooth when said motive source is operating; and a filament support positioned at said second end of said housing to support said flossing filament and having a passageway therethrough with said flossing filament extending through said passageway and movably disposed therein, said flossing filament being rotatably disposed in said passageway of said filament support.

71. The apparatus of claim 70 wherein said motive source is rotatably connected by said coupling to said base portion, and said filament support is positioned and supports said flossing filament at a location between said free-end portion and said base portion of said flossing filament.

72. The apparatus claim 70 wherein said flossing filament is loosely disposed within said passageway.

73. The apparatus of claim 70 wherein said elongated tooth engagement portion of said intermediate portion is located exterior of said filament support and said intermediate portion extending beyond said filament support has sufficient flexibility to bend outward while rotating in response to the centrifugal force thereon resulting from rotation of said flossing filament by said motive source.

74. The apparatus of claim 70 wherein said motive source provides a unidirectional rotational drive to said flossing filament to produce said flossing motion in response to operation of said motive source.

75. Apparatus for cleaning the surfaces of teeth underlying the inter-dental papilla portion of the gums in a human mouth by effecting a flossing action, comprising:

a motive source;

a flexible, resilient flossing filament;

said flossing filament including a base portion, a free-end portion, and a non-abrasive elongated intermediate portion located between said base portion and said free-end portion;

said intermediate portion and said free-end portion being capable of being received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;

at least said intermediate portion being capable of being received in the sulcus between a tooth and the adjacent inter-dental papilla portion of the gum for effecting the flossing action therein;

a filament support positioned between said free-end portion and said base portion of said flossing filament to support said flossing filament at a location therealong, said free-end portion and an elongated portion of said intermediate portion extending beyond said filament support for engagement with the tooth when said motive source is operating; and a coupling connecting said flossing filament to said motive source and providing driving force to said flossing filament out of longitudinal alignment with said flossing filament to impart said flossing motion to said intermediate portion, said intermediate portion extending beyond said filament support having sufficient flexibility to bend outward under said driving force applied to said flossing filament, said coupling providing said driving force with sufficient force to bend outward said intermediate portion extending beyond said filament support and move said bent intermediate portion about to produce said flossing movement of said intermediate portion.

76. The apparatus of claim 75 wherein said filament support has a passageway therethrough and said flossing filament extends and is movably disposed in said passageway.

77. Apparatus for cleaning the surfaces of teeth underlying the inter-dental papilla portion of the gums in a human mouth by effecting a flossing action, comprising:

a flexible, resilient flossing filament;

said flossing filament including a base portion, a free-end portion, and a non-abrasive elongated intermediate portion located between said base portion and said free-end portion;

said intermediate portion and said free-end portion being capable of being received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;

at least said intermediate portion being capable of being received in the sulcus between a tooth and the adjacent inter-dental papilla portion of the gum for effecting the flossing action therein;

a motive source, said motive source producing an output drive; and a coupling connecting said flossing filament to said motive source to impart said flossing motion to said intermediate portion, said coupling translating said output drive into an oscillatory drive and supplying said oscillatory drive to said flossing filament to move said flossing filament along a generally translatory path of travel to produce said flossing motion of said intermediate portion.

78. The apparatus of claim 77 wherein said output drive of said motive source is a rotational drive, and said coupling translates said rotational drive into said oscillatory drive.

79. Apparatus for cleaning the surfaces of teeth underlying the inter-dental papilla portion of the gums in a human mouth by effecting a flossing action, comprising:

a flexible, resilient filament;

said flossing filament including a base portion, a free-end portion, and a non-abrasive, elongated intermediate portion located between said base portion and said free-end portion;

said intermediate portion and said free-end portion being sized to be received between adjacent teeth without traversing any contact areas between the teeth from at least the front of the mouth, at least said intermediate portion having sufficient flexibility and resiliency to be capable of effecting effect the flossing action therebetween by imparting a flossing motion to said intermediate portion;

at least said intermediate portion being sized to be received in the sulcus between a tooth and the adjacent inter-dental papilla portion of the gum for effecting the flossing action therein;

a motive source, said motive source producing an output drive; and a coupling connecting said flossing filament to said motive source and imparting said flossing motion to said intermediate portion in response to operation of said motive source, said coupling providing an oscillatory drive to said flossing filament to move said flossing filament along a generally translatory path of travel to produce said flossing motion of said intermediate portion.

80. The apparatus of claim 79 wherein said motive source is a motor producing a rotational drive as said output drive and said coupling translates said rotational drive into said oscillatory drive.

81. Apparatus for cleaning the surfaces of teeth underlying the inter-dental papilla portion of the gums in a human mouth by effecting a flossing action, comprising:

a flexible, resilient, non-abrasive flossing filament;

said flossing filament including a base portion, a free-end portion, and an elongated intermediate portion located between said base portion and said free-end portion;

said intermediate portion and said free-end portion being sized to be received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;

at least said intermediate portion being sized to be received in the sulcus between a tooth and the adjacent inter-dental papilla portion of the gum for effecting the flossing action therein;

a motive source; and a coupling connecting said base portion of said flossing filament to said motive source and imparting said flossing motion to said intermediate portion in response to operation of said motive source, said coupling imparting said flossing motion to said intermediate portion with a rotational component.

82. Apparatus for cleaning the surfaces of teeth underlying the inter-dental papilla portion of the gums in a human mouth by effecting a flossing action, comprising:
- a flexible, resilient flossing filament having sufficient stiffness to be self-supporting;
- said flossing filament including a base portion, a free-end portion, and a non-abrasive elongated intermediate portion located between said base portion and said free-end portion;
- said intermediate portion and said free-end portion being sized to be received between adjacent teeth without traversing any contact areas between the teeth from at least the front of the mouth, at least said intermediate portion being composed of a material having sufficient flexibility and resiliency to effect the flossing action therebetween without damage to the teeth by imparting a flossing motion to said intermediate portion, said intermediate portion extending along a longitudinal extension line when not moving;
- at least said intermediate portion being sized to be received in the sulcus between a tooth and the adjacent inter-dental papilla portion of the gum for effecting the flossing action therein;
- a motive source; and
- a coupling connecting said base portion of said flossing filament to said motive source and moving said intermediate portion among a plurality of positions substantially out of alignment with said longitudinal line to impart said flossing motion to said intermediate portion.

83. Apparatus for cleaning the surfaces of teeth underlying the inter-dental papilla portion of the gums in a human mouth by effecting a flossing action, comprising:
- a flexible, resilient, non-abrasive flossing filament;
- said flossing filament including a base portion, a free-end portion, and an elongated intermediate portion located between said base portion and said free-end portion;
- said intermediate portion and said free-end portion being sized to be received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;
- at least said intermediate portion being sized to be received in the sulcus between a tooth and the adjacent inter-dental papilla portion of the gum for effecting the flossing action therein;
- a motive source, said motive source being rotatably connected by said coupling to said base portion to provide rotational drive to said flossing filament to produce said flossing motion; and
- a coupling connecting said base portion of said flossing filament to said motive source and imparting said flossing motion to said intermediate portion in response to operation of said motive source.

84. Apparatus for cleaning the surfaces of teeth underlying the inter-dental papilla portion of the gums in a human mouth by effecting a flossing action, comprising:
- a flexible, resilient flossing filament,
- said flossing filament including a base portion, a free-end portion, and a non-abrasive elongated intermediate portion located between said base portion and said free-end portion;
- said intermediate portion and said free-end portion being capable of being received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;
- at least said intermediate portion being capable of being received in the sulcus between a tooth and the adjacent inter-dental papilla portion of the gum for effecting the flossing action therein;
- a motive source; and
- a coupling connecting said flossing filament to said motive source to impart said flossing motion to said intermediate portion, said coupling imparting said flossing motion to said intermediate portion with a rotational component.

85. Apparatus for cleaning the surfaces of teeth underlying the inter-dental papilla portion of the gums in a human mouth by effecting a flossing action, comprising:
- a flexible, resilient, non-abrasive flossing filament;
- said flossing filament including a base portion, a free-end portion, and an elongated intermediate portion located between said base portion and said free-end portion;
- said intermediate portion and said free-end portion being sized to be received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;
- at least said intermediate portion being sized to be received in the sulcus between a tooth and the adjacent inter-dental papilla portion of the gum for effecting the flossing action therein;
- a motive source, said motive source producing a rotational output drive; and
- a coupling connecting said base portion of said flossing filament to said motive source and imparting said flossing motion to said intermediate portion in response to operation of said motive source, said motive source being connected by said coupling to said base portion to supply said rotational output drive to said flossing filament to move said flossing filament along a generally conical path of travel to produce said flossing motion of said intermediate portion.

86. Apparatus for cleaning the surfaces of teeth underlying the inter-dental papilla portion of the gums in a human mouth by effecting a flossing action, comprising:
- a flexible, resilient flossing filament;
- said flossing filament including a base portion, a free-end portion, and a non-abrasive elongated intermediate portion located between said base portion and said free-end portion;
- said intermediate portion and said free-end portion being capable of being received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;

at least said intermediate portion being capable of being received in the sulcus between a tooth and the adjacent inter-dental papilla portion of the gum for effecting the flossing action therein;

a motive source, said motive source producing a rotational output drive; and a coupling connecting said flossing filament to said motive source to impart said flossing motion to said intermediate portion, said motive source being connected by said coupling to said flossing filament to supply said rotational output drive to said flossing filament to move said flossing filament along a generally conical path of travel to produce said flossing motion of said intermediate portion.

87. Apparatus for cleaning the surfaces of teeth underling the inter-dental papilla portion of the gums in a human mouth by effecting a flossing action, comprising:

a flexible, resilient flossing filament;

said flossing filament including a base portion, a free-end portion, and a non-abrasive elongated intermediate portion located between said base portion and said free-end portion;

said intermediate portion and said free-end portion being capable of being received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;

at least said intermediate portion being capable of being received in the sulcus between a tooth and the adjacent inter-dental papilla portion of the gum for effecting the flossing action therein;

a motive source, said motive source producing a rotational output drive, and a coupling connecting said flossing filament to said motive source to impart said flossing motion to said intermediate portion, said coupling translating said rotational drive into an oscillatory drive and supplying said oscillatory drive to said flossing filament to produce said flossing motion of said intermediate portion.

88. Apparatus for cleaning the surfaces of teeth underlying the inter-dental papilla portion of the gums in a human mouth by effecting a flossing action, comprising:

a flexible, resilient flossing filament;

said flossing filament including a base portion, a free-end portion, and a non-abrasive elongated intermediate portion located between said base portion and said free-end portion;

said intermediate portion and said free-end portion being capable of being received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;

at least said intermediate portion being capable of being received in the sulcus between a tooth and the adjacent inter-dental papilla portion of the gum for effecting the flossing action therein;

a motive source, said motive source producing an output drive; and a coupling connecting said flossing filament to said motive source to impart said flossing motion to said intermediate portion, said coupling translating said output drive into a rotational drive and supplying said rotational drive to said flossing filament to produce said flossing motion of said intermediate portion.

89. Apparatus for cleaning the surfaces of teeth underlying the inter-dental papilla portion of the gums in a human mouth by effecting a flossing action, comprising:

a flexible, resilient, non-abrasive flossing filament, said flossing filament including a base portion, a free-end portion, and an elongated intermediate portion located between said base portion and said free-end portion;

said intermediate portion and said free-end portion being sized to be received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;

at least said intermediate portion being sized to be received in the sulcus between a tooth and the adjacent inter-dental papilla portion of the gum for effecting the flossing action therein;

a motive source, said motive source producing a rotational output drive; and a coupling connecting said base portion of said flossing filament to said motive source and imparting said flossing motion to said intermediate portion in response to operation of said motive source, said coupling translating said rotational drive into an oscillatory drive and supplying said oscillatory drive to said base portion to produce said flossing motion of said intermediate portion.

90. Apparatus for cleaning the surfaces of teeth underlying the inter-dental papilla portion of the gums in a human mouth by effecting a flossing action, comprising:

a flexible flossing filament having sufficient stiffness to be self-supporting;

said flossing filament including a base portion, a free-end portion, and a non-abrasive intermediate portion located between said base portion and said free-end portion;

said intermediate portion and said free-end portion being sized to be received between adjacent teeth without traversing any contact areas between the teeth from at least the front of the mouth, said intermediate portion being sufficiently flexible to effect the flossing action therebetween by imparting a flossing motion to said intermediate portion;

at least said intermediate portion being sized to be received in the sulcus between a tooth and the adjacent inter-dental papilla portion of the gum for effecting the flossing action therein;

a motive source; and a coupling connecting said flossing filament to said motive source and applying a moving force to said flossing filament with at least one of a translational and a rotational component to impart said flossing motion to said intermediate portion in response to operation of said motive source.

91. Apparatus for cleaning the surfaces of teeth underlying the inter-dental papilla portion of the gums in a human mouth by effecting a flossing action, comprising:

a flexible, resilient, non-abrasive flossing filament;

said flossing filament including a base portion, an intermediate portion, and a tip;

said intermediate portion and said tip sized to be received between adjacent teeth without traversing any contact areas between the teeth from at least the front of the mouth, at least said intermediate portion having sufficient flexibility and resiliency to effect the flossing action therebetween by imparting a flossing motion to said intermediate portion, said intermediate portion extending along a longitudinal extension line when not moving;

at least said intermediate portion being sized to be received in the sulcus between a tooth and the adjacent inter-dental papilla portion of the gum for effecting the flossing action therein;

a motive source to supply drive force to said flossing filament; and a coupling connecting said flossing filament to said motive source and moving said flossing filament such that said intermediate portion moves alone a plurality of positions substantially out of alignment with said longitudinal line to impart said flossing motion to said intermediate portion, said coupling transmitting sufficient drive force supplied by said motive source to said flossing filament to clean the surfaces of teeth without damaging the teeth.

92. Apparatus for cleaning the surfaces of teeth underlying the inter-dental papilla portion of the gums in a human mouth by effecting a flossing action, comprising:

a motive source;

a flexible, resilient flossing filament;

said flossing filament including a base portion, a free-end portion, and a non-abrasive intermediate portion located between said base portion and said free-end portion;

said intermediate portion and said free-end portion being sized to be received between adjacent teeth without traversing any contact areas between the teeth from at least the front of the mouth, at least said intermediate portion having sufficient flexibility and resiliency to effect the flossing action therebetween by producing a flossing motion when driven by said motive source, said intermediate portion extending alone a longitudinal line when not driven by said motive source;

at least said intermediate portion being sized to be received in the sulcus between a tooth and the adjacent inter-dental papilla portion of the gum for effecting the flossing action therein; and a coupling drivingly connecting said flossing filament to said motive source and moving said flossing filament with a component of motion out of alignment with said longitudinal line to produce said flossing motion of said intermediate portion.

93. Apparatus for cleaning the surfaces of teeth underlying the inter-dental papilla portion of the gums in a human mouth by effecting a flossing action, comprising:

a flexible, resilient, non-abrasive flossing filament;

said flossing filament including a base portion, an intermediate portion, and a tip;

said intermediate portion and said tip being capable of being received between adjacent teeth without traversing any contact areas between the teeth from at least the front of the mouth and being capable of effecting the flossing action therebetween;

at least said intermediate portion being capable of being received in the sulcus between a tooth and the adjacent inter-dental papilla portion of the gum for effecting the flossing action therein;

a motor producing a rotational output drive; and a coupling connecting said base portion of said flossing filament to said motor, said coupling converting said rotational output drive into a moving force applied to said flossing filament which moves said flossing filament along a path of travel substantially out of alignment with said flossing filament when at rest to effect a flossing motion of said flossing filament.

94. Apparatus for cleaning the surfaces of teeth underlying the inter-dental papilla portion of the gums in a human mouth by effecting a flossing action, comprising:

a flexible, resilient, non-abrasive flossing filament;

said flossing filament including a base portion, a free-end portion, and an elongated intermediate portion located between said base portion and said free-end portion;

said intermediate portion and said free-end portion being sized to be received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;

at least said intermediate portion being sized to be received in the sulcus between a tooth and the adjacent inter-dental papilla portion of the gum for effecting the flossing action therein;

a motive source, said motive source producing an output drive; and a coupling connecting said base portion of said flossing filament to said motive source and imparting said flossing motion to said intermediate portion in response to operation of said motive source, said coupling translating said output drive into a rotational drive and supplying said rotational drive to said base portion to produce said flossing motion of said intermediate portion.

95. Apparatus for cleaning the surfaces of teeth underlying the inter-dental papilla portion of the gums in a human mouth by effecting a flossing action, comprising:

a flexible, resilient flossing filament;

said flossing filament including a base portion, a free-end portion, and a non-abrasive elongated intermediate portion located between said base portion and said free-end portion;

said intermediate portion and said free-end portion being sized to be received between adjacent teeth without traversing any contact areas between the teeth from at least the front of the mouth, at least said intermediate portion having sufficient flexibility and resiliency to effect the flossing action therebetween by imparting a flossing motion to said intermediate portion;

at least said intermediate portion being sized to be received in the sulcus between a tooth and the adjacent inter-dental papilla portion of the gum for effecting the flossing action therein;

a motor producing an output drive; and a coupling connecting said flossing filament to said motor to transmit said output drive to said flossing filament and thereby move said flossing filament with a component of motion which imparts said flossing motion to said intermediate portion.

96. Apparatus for cleaning the surfaces of teeth underlying the inter-dental papilla portion of the gums in a human mouth by effecting a flossing action, comprising:

a flexible, resilient flossing filament;

said flossing filament including a base portion, a free-end portion, and an intermediate portion located between said base portion and said free-end portion;

said intermediate portion and said free-end portion being sized to be received between adjacent teeth without traversing any contact areas between the teeth from at least the front of the mouth, at least said intermediate portion having sufficient flexibility and resiliency to be capable of effecting the flossing action therebetween by imparting a flossing motion to said intermediate portion;

at least said intermediate portion being sized to be received in the sulcus between a tooth and the adjacent inter-dental papilla portion of the gum for effecting the flossing action therein;

a motive source; and a coupling connecting said base portion of said flossing filament to said motive source and moving said flossing filament with a rotational component to impart said flossing motion to said intermediate portion in response to operation of said motive source.

97. Apparatus for cleaning the surfaces of teeth underlying the inter-dental papilla portion of the gums in a human mouth by effecting a flossing action, comprising:

a flexible, resilient flossing filament having sufficient stiffness to be self supporting;

said flossing filament including a base portion, a free-end portion, and an intermediate portion located between said base portion and said free-end portion;

said intermediate portion and said free-end portion being capable of being received between adjacent teeth without traversing any contact areas between the teeth from at least the front of the mouth, at least said intermediate portion being composed of a material having sufficient flexibility and resiliency to be capable of effecting the flossing action therebetween without damage to the teeth by imparting a flossing motion to said intermediate portion;

at least said intermediate portion being capable of being received in the sulcus between a tooth and the adjacent inter-dental papilla portion of the gum for effecting the flossing action therein;

a motive source; and a coupling connecting said base portion of said flossing filament to said motive source and moving said flossing filament with a rotational component to impart said flossing motion to said intermediate portion.

98. Apparatus for cleaning the surfaces of teeth underlying the inter-dental papilla portion of the gums in a human mouth by effecting a flossing action, comprising:

a flexible, resilient flossing filament;

said flossing filament including a base portion, a free-end portion, and an intermediate portion located between said base portion and said free-end portion;

said intermediate portion and said free-end portion being capable of being received between adjacent teeth without traversing any contact areas between the teeth from at least the front of the mouth and being capable of effecting the flossing action therebetween;

at least said intermediate portion being capable of being received in the sulcus between a tooth and the adjacent inter-dental papilla portion of the gum for effecting the flossing action therein;

a motive source; and a coupling connecting said flossing filament to said motive source to effect motion of said intermediate portion with a rotational component.

99. Apparatus for cleaning the surfaces of teeth underlying the inter-dental papilla portion of the gums in a human mouth by effecting a flossing action, comprising:

a flexible flossing filament having sufficient stiffness to be self supporting;

said flossing filament including a base portion, a free-end portion, and an intermediate portion located between said base portion and said free-end portion;

said intermediate portion and said free-end portion being capable of being received between adjacent teeth without traversing any contact areas between the teeth from at least the front of the mouth, said intermediate portion being capable of effecting the flossing action therebetween by imparting a flossing motion to said intermediate portion;

at least said intermediate portion being capable of being received in the sulcus between a tooth and the adjacent inter-dental papilla portion of the gum for effecting the flossing action therein;

a motive source; and a coupling connecting said flossing filament to said motive source and moving said flossing filament with a rotational component to impart said flossing motion to said intermediate portion in response to operation of said motive source.

100. Apparatus for cleaning the surfaces of teeth underlying the inter-dental papilla portion of the gums in a human mouth by effecting a flossing action, usable with a motive source, the apparatus comprising:

a flexible flossing filament having sufficient stiffness to be self-supporting;

said flossing filament including a base portion, a free-end portion, and a non-abrasive intermediate portion located between said base portion and said free-end portion;

said intermediate portion and said free-end portion having a thickness sufficiently small to be received between adjacent teeth without traversing any contact areas between the teeth from at least the front of the mouth, at least said intermediate portion having sufficient flexibility and resiliency to effect the flossing action therebetween by imparting a flossing motion to said intermediate portion;

at least said intermediate portion having a sufficiently small thickness and a configuration to be received in the sulcus between a tooth and the adjacent inter-dental papilla portion of the gum for effecting the flossing action therein, said intermediate portion having sufficient stiffness to be inserted by itself endwise between adjacent teeth and into the sulcus without substantial deformation of shape;

said base portion being configured to be releasably connected to the motive source such that the motive source imparts said flossing motion to said intermediate portion in response to operation of the motive source;

a filament receiver having a support portion thereof supporting said flossing filament so as to allow said intermediate portion to be moved with said flossing motion; and said filament being uncoiled and having an uncoiled length between said base portion and said free-end portion sized to position said base portion at the motive source for connection thereto and said free-end portion outward of said filament receiver when said filament extends directly from said base portion at the motive source, through and beyond said filament receiver to said free-end portion, with said free-end portion and at least a portion of said intermediate portion located outward of said filament receiver.

101. The apparatus of claim 100 for use with a housing and a coupling wherein said filament receiver has a first portion removably attached to a housing and a second portion, said filament receiver having a first aperture in said first portion and a second aperture in said second portion with a passageway extending between said first and second apertures, said flossing filament being rotatably disposed in said filament receiver passageway, said flossing filament extending through said second aperture with said filament free-end portion and at least a portion of said intermediate portion positioned outward of said filament receiver, and extending through said first aperture with said filament base portion positioned to be releasably connected by the coupling to the motive source to rotate said flossing filament within said filament receiver passageway to impart said flossing motion to said portion of said intermediate portion positioned outward of said filament receiver when said first end of said filament receiver is attached to the housing.

102. Apparatus for cleaning the surfaces of teeth underlying the inter-dental papilla portion of the gums in a human mouth by effecting a flossing action, usable with a drive assembly and a filament receiver having a passageway therethrough and an outward end, the apparatus comprising:

a flexible and resilient flossing filament having sufficient stiffness to be self-supporting and rotated as a unit along a full length thereof;

said flossing filament including a base portion, a free-end portion, and an intermediate portion located between said base portion and said free-end portion;

said intermediate portion and said free-end portion having a thickness sufficiently small to be received between adjacent teeth without traversing any contact areas between the teeth from at least the front of the mouth and being sufficiently flexible and resilient to effect the flossing action therebetween;

at least said intermediate portion having a sufficiently small thickness and a configuration to be received in the sulcus between a tooth and the adjacent inter-dental papilla portion of the gum for effecting the flossing action therein, said intermediate portion and said free-end portion having sufficient stiffness to be inserted by themselves endwise between adjacent teeth and into the sulcus without substantial deformation of shape;

said base portion being configured to be releasably connected to the drive assembly to effect motion of said intermediate portion to produce the flossing action; and said filament being uncoiled and having an uncoiled length between said base portion and said free-end portion sized to position said base portion at the drive assembly for connection thereto and said free-end portion outward of said outward end of said filament receiver when said filament extends directly from said base portion at the drive assembly, through the receiver passageway and beyond the receiver outward end to said free-end portion, with said free-end portion and at least a portion of said intermediate portion located outward of the receiver outward end.

* * * * *